United States Patent [19]
Gorog et al.

[11] Patent Number: 5,665,311
[45] Date of Patent: Sep. 9, 1997

[54] BLOOD TESTING DEVICE

[76] Inventors: Peter Gorog; Iren Kovacs, both of 20 Grenville Court, Lymer Avenue, Dulwich Wood Park, London SE19 1LS, England

[21] Appl. No.: 314,663
[22] PCT Filed: Sep. 10, 1987
[86] PCT No.: PCT/GB87/00633
    § 371 Date: Feb. 3, 1989
    § 102(e) Date: Feb. 3, 1989
[87] PCT Pub. No.: WO88/02116
    PCT Pub. Date: Mar. 24, 1988

[30] Foreign Application Priority Data

Sep. 10, 1986 [GB] United Kingdom ............ 8621757

[51] Int. Cl.[6] ........................................ G01N 33/49
[52] U.S. Cl. ........................ 422/73; 427/81; 436/65; 436/148
[58] Field of Search ............. 422/73, 81, 82.13; 436/69, 148; 73/64.1; 128/760, 763

[56] References Cited

U.S. PATENT DOCUMENTS

| | | | |
|---|---|---|---|
| 3,699,437 | 10/1972 | Ur | 324/65 |
| 3,720,097 | 3/1973 | Kron | 73/55 |
| 3,900,290 | 8/1975 | Hornstra | 73/64.1 |
| 4,213,456 | 7/1980 | Bottger | 128/763 |
| 4,319,194 | 3/1982 | Cardinal et al. | 128/637 |
| 4,604,894 | 8/1986 | Kratzer et al. | 436/69 |
| 4,634,679 | 1/1987 | Horres | 436/63 |
| 4,780,418 | 10/1988 | Kratzer | 436/69 |

*Primary Examiner*—Timothy McMahon
*Attorney, Agent, or Firm*—Cushman Darby & Cushman Intellectual Property Group of Pillsbury Madison & Sutro, LLP

[57] ABSTRACT

An apparatus for measuring physical properties of blood is disclosed. Two reservoirs are provided connected to a receptacle means by at least two elongated tubes. A punching station located along the two tubes permits the simultaneous punching of holes to simulate bleeding in the tubes. The bleeding of the tubes is monitored to indicate the haemostasis properties of blood flowing through the elongated tubes. Monitoring is effected by measuring the downstream pressure of a punched tube. Alternate embodiments include the addition of third channel having a collagen material within the channel. Platelet aggregation on the collagen material is observed as a measure of haemostasis properties of the blood.

12 Claims, 4 Drawing Sheets

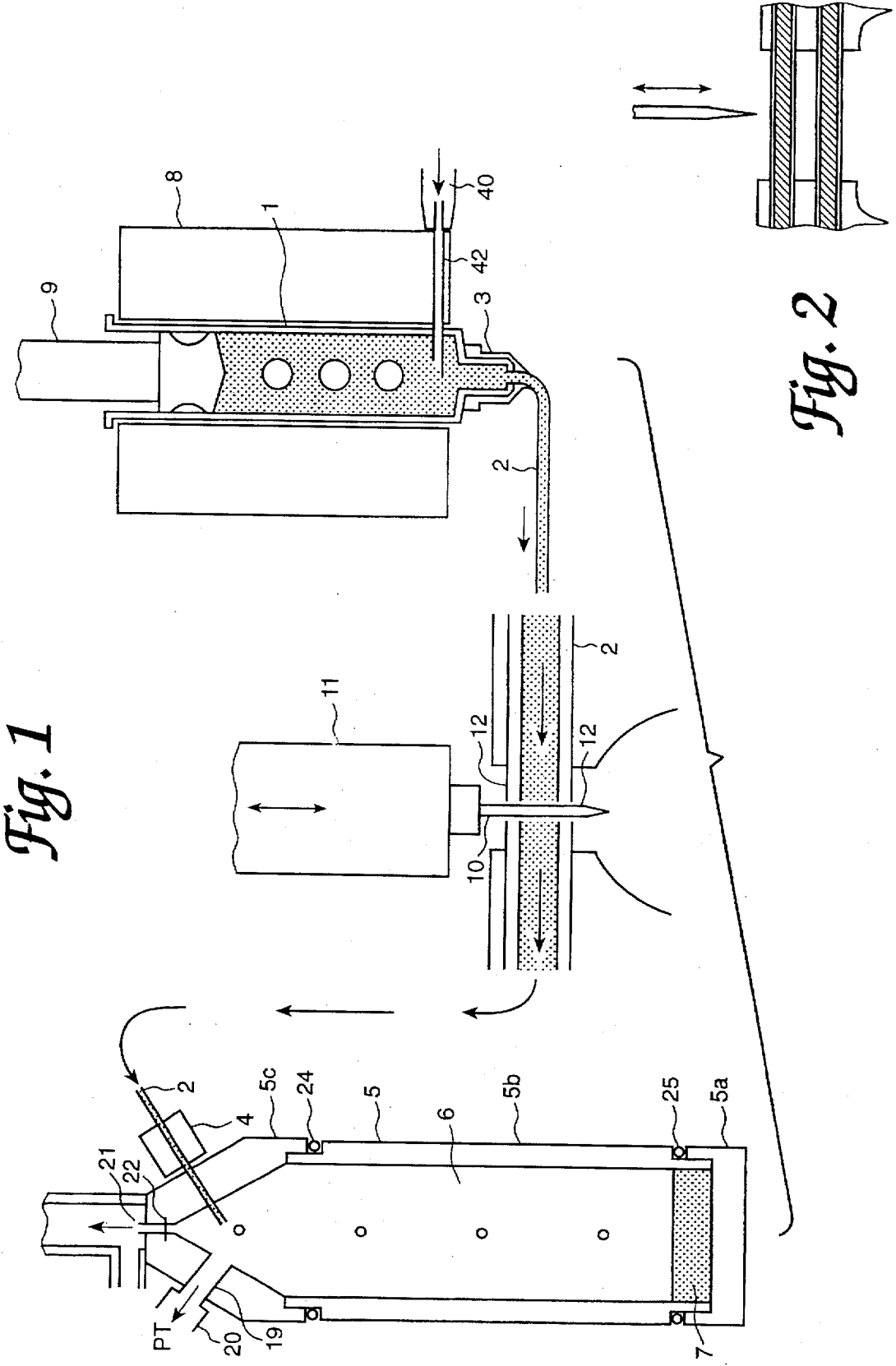

BLOOD TESTING DEVICE

This invention relates to the measurement of various haemostasis, clotting, and the like properties of blood, and specifically to apparatus enabling measurements of such quantities to be made on blood. A device of this kind is disclosed in European Patent Specification No. 129425.

In that specification there is disclosed apparatus for the investigation of blood, comprising a columnar reservoir for holding the blood, an elongate tube leading from the reservoir to a waste blood holding vessel, and means for introducing into the reservoir a fluid immiscible with blood to displace the blood through the tube, while simultaneously stirring the blood in the columnar reservoir (hereinafter referred to as "apparatus of the type described").

I have now discovered a number of modifications and improvements to the apparatus disclosed in European Patent Specification No. 129425, which not only enable more reliable and more reproducible measurements to be made of clotting and heamostasis but also enable a number of other quantities to be measured.

SUMMARY OF THE INVENTION

In accordance with a first aspect of the invention, apparatus of the type described includes a pair of parallel channels, each channel comprising a columnar reservoir, elongate tube, waste blood holding vessel, and means for introducing a displacing fluid, as described above.

The use of two parallel channels enables a number of measurements to be made which are not possible with a simple single channel instrument. For example, in a preferred embodiment of this aspect of the invention, each channel has a punching station, at which, as disclosed in European Patent Specification No. 129425, a through-hole is punched through the elongate tube, to simulate bleeding. So that the size of the holes in the two tubes is exactly the same, both holes may be punched by a single parallel-sided punching needle. In an alternative embodiment, two exactly similar needles may be provided at corresponding places in the tubes of the two channels.

The use of parallel channels is particularly advantageous, because it enables measurements of clotting and haemostasis is kinds to be carried out on whole blood. Thus, in one embodiment, the columnar reservoir of both channels is filled with native blood, and caused to flow through the respective elongate tube, by displacement. Both channels are pierced, and the time it takes for haemostasis to occur (i.e. the formation of a platelet plug in the two holes) is measured in both channels. Because the test is carried out in both channels using whole blood, the platelet plug formed simulates very closely platelet plugs formed in arterial bleeding.

An anticoagulant agent is then introduced in to the blood flowing in one of the channels. This prevents the blood flowing in that channel from clotting, so that thrombolysis of the platelet plug in that channel can be investigated but does not interfere with the haemostatic plug formation because the haemostatic plug has already been formed when the anticoagulant is introduced. A preferred anticoagulant is heparin, because of its low interference with the thrombolytic process.

After a period of time the blood in the channel which is not anticoagulated will clot, and this can be measured by appropriate pressure transducers. In the channel to which the anticoagulant has been added, the platelet plug will eventually dissolve, and therefore thrombolysis time can be measured.

The two-channel instrument of the first embodiment of the present invention is also useful in other clinical diagnostic techniques, for example to determine the effects of various pharmaceuticals substances on clotting, haemostasis and thrombolysis. Native blood containing saline (control) may be utilised in one channel of the apparatus, and identical blood containing the pharmaceutical substance to be investigated in the other, and thus the effect on the various properties of the blood can be monitored under closely controlled conditions.

In a second aspect, the invention is concerned with the effect of various substances, for example collagen, on haemostasis/thrombosis. For example, a small piece of collagen, such as a piece of a surgical suture, may be placed within the elongate tube leading from the columnar reservoir to the blood holding vessel of apparatus of the type described, and the blood caused to flow over the substance.

The mechanism of platelet thrombus formation on the surface of substances such as collagen is similar to that which occurs during the normal passage of blood through injured blood vessels in the body. Collagen fibres are exposed when blood vessels are ruptured and it is of considerable clinical interest to investigate in detail the effect of collagen during thrombus formation. In particular, it has been established by electron micrography that thrombus formation takes place by means of the build up of a monolayer of platelets on the collagen surface, followed by subsequent platelet adhesion to succeeding layers. Electron micrography is an expensive and time consuming technique, and in a second aspect of the invention, a method and apparatus are provided for enabling the investigation of platelets on substances such as collagen or other biocompatible materials to be carried out, using relatively simply apparatus.

In accordance with this aspect of the invention, a piece of the substance such as collagen is provided in the elongate tube of the apparatus, and the progress of thrombus formation is followed by observing blood flow in the tube, for example by the measurement of pressure, as disclosed hereinafter, as the formation of a thrombus on the substance causes a characteristic pattern of occlusion of the tube.

In accordance with a third aspect of the invention, three parallel channels may be provided, to enable the effect of substances such as collagen on thrombus formation to be determined, whilst other measurements are also being performed, for example haemostasis and blood clotting measurements.

A fourth aspect of the invention relates to the method by which blood flow in apparatus of the type described is measured and controlled. In European Patent Application No. 129425, a pressure transducer is utilised, to measure variation of pressure in the blood, as the holes are punched, and subsequently occluded by platelet plugs. The pressure transducer however is positioned upstream of the punching station, so that the only measurement possible with regarding to clotting in the tube is the point at which blood flow in the tubes ceases completely. In accordance with the fourth aspect of the invention, apparatus of the type described includes a pressure transducer downstream of the elongate tube, and preferably disposed so as to measure pressure in the waste blood holding vessel, whereby the process of blood clotting can be followed. Thus, as the blood clot in the tube grows in size, flow through the tube diminishes steadily, and thus the pressure in the waste blood reservoir falls. As in European Patent Application No. 129425, the waste holding vessel is; in this embodiment, filled with a fluid immiscible with the blood, which is displaced by the entry of the blood.

A fifth aspect of the invention is concerned with the mechanism for causing the blood to pass through the elongate tube. In European Patent Application No. 129425, the blood is displaced by a fluid immiscible therewith, for example paraffin oil, which is supplied to the columnar container using a syringe pump. This arrangement is somewhat disadvantageous in practice, because it tends to result in a pressure profile which varies unacceptably, and is also rather difficult to control.

In accordance with a sixth aspect of the invention, apparatus of the type described includes means for introducing the immiscible fluid into the columnar container, comprising a pressurisable vessel for the immiscible fluid, means for applying a constant pressure head to the pressurisable container, and a capillary tube leading from the pressurisable vessel to the columnar container, the capillary tube having a resistance to flow substantially greater than that of the tube leading from the columnar container to the waste blood holding vessel. Because in this arrangement, the greater part of the pressure drop across the apparatus takes place across the capillary tube, rather than the tube which is pierced, a constant pressure applied to the pressure vessel results in a substantially contant flow of the displacing fluid into the columnar container. Thus, the flow of blood through the apparatus can be readily controlled, by controlling the pressure in the pressurisable container. This may be applied using, for example, a twin-head pump, or a gas cylinder.

A seventh aspect of the invention relates to the nature of the columnar container itself. In the apparatus disclosed in European Patent Specification No. 129425, the columnar container is essentially a tube provided with a fluid inlet and a fluid outlet at its bottom part, for, respectively, introduction of the displacing fluid, and the outflow of blood. One disadvantage of this arrangement is that it necessitates transfer of the blood from one container to another, after it has been taken from the patient, and this can result in the initiation of the clotting process. Furthermore, the tube arrangement includes a number of sharp corners over which the blood must flow, and these and the turbulence caused also can initiate the clotting/haemostasis process. In the seventh aspect of the invention, the columnar container is preferably a plastics syringe, which can be used to take a blood sample from a patient in the ordinary way, and from which the hypodermic needle can then be removed, so that the elongate tube leading to the waste blood holding vessel can be attached. The apparatus preferably includes a mounting block for the syringe, which may include temperature control means, for example a water jacket, or a thermostatically controlled heating element. In devices according to the invention having two or three parallel channels, the mounting block will generally be adapted for mounting a syringe for each channel.

The support block may also preferably comprise a port or septum, so that a hypodermic needle may be introduced into the syringe, through its wall, for introduction of the displacement fluid. The displacement fluid will normally be less dense than blood, and accordingly the port is preferably positioned close to the bottom of the hypodermic syringe, so that introduction of the displacement fluid causes effective stirring of the blood. The elongate tube leading from the syringe to the waste blood vessel is preferably attached by a LUER-type fitting, and by this method virtually all parts of the apparatus which come into contact with blood are rendered disposable. Thus, the syringe, tubing and waste blood holding vessel may all be discarded after use.

Yet a further aspect of the invention is concerned with the investigation of thrombolysis. As indicated above, by carrying out the second phase of the measurements on anticoagulated blood, it is possible to follow the progress of thrombolysis in blood, and to investigate the effect of various agents on thrombolysis. Although haemostatis and clotting are relatively quick to occur, thrombolysis will generally require a much longer time for completion, for example from fifteen to forty minutes. If the blood is caused to flow in the elongate tube for the whole of this period, substantial quantities of blood are required. However, once the anticoagulant has been added, it is no longer necessary for the flow of blood to be maintained in the tube, provided that the pressure of the blood remains constant.

Accordingly, in this further aspect of the invention, there is provided a valve, for example a needle valve, for closing the outlet of the waste blood holding vessel, so that after anticoagulated blood has passed through the whole of the elongate tube, the valve can be closed, such that pressure in the system can be maintained, without the loss of blood therefrom. The progress of thrombolysis can then be measured, as above, using a pressure transducer in the waste blood holding vessel. This arrangement is particularly advantageously used with the arrangement described above of a pressurised vessel for driving the displacement fluid in the columnar blood container. In this preferred embodiment, means may be provided for reducing the pressure applied to the pressurisable vessel, when the valve is closed. Since the internal pressure in the blood-containing parts of the system (the columnar container, elongate tube and waste blood holding vessel) is substantially below that in the pressurisable container, closing of the valve would result in the overall rise in pressure in the system, because of equalisation of the pressure in the blood-containing parts, and the displacement fluid containing parts. In this preferred embodiment of the invention therefore, means are preferably provided for applying a reduced pressure to the displacement fluid, after closure of the valve. In one embodiment, the means for applying the reduced pressure may take the form of two pressurisable containers, pressurised to different pressures, and alternatively switchable to provide the pressure to drive the displacement fluid.

Although all of the various aspects of the invention are preferably embodied in the same apparatus, it should be understood that each aspect may be utilised independently, or the various aspects may be utilised in any desired combination.

DESCRIPTION OF THE FIGURES

A particularly preferred embodiment of apparatus incorporating all of the above aspects of the invention will now be described, with reference to the accompanying drawings, in which:

FIG. 1 is a schematic diagram showing one channel of a two-channel blood analysis device, FIG. 2 is a schematic diagram of the punching station of a two-channel device.

DESCRIPTION OF THE PREFERRED EMBODIMENT

Figure 3:
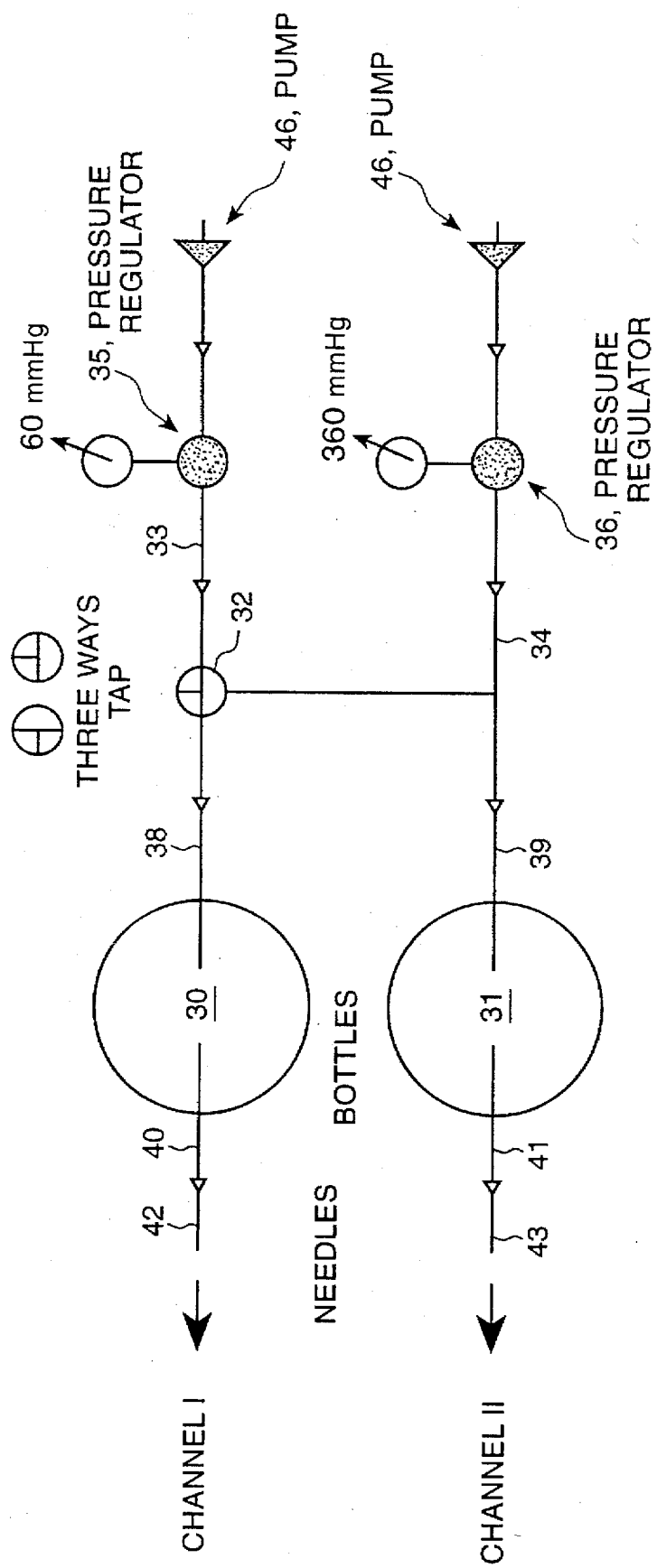
FIG. 3 shows a preferred pressurised vessel arrangement.

Referring first to FIG. 1, one channel of a two-channel instrument comprises a columnar container for holding blood, in the form of a 2 ml hypodermic syringe 1, made of a disposable plastics material. A elongate polyethylene tube, having an internal diameter of 0.5 mm, and a length of approximately 30 cm is connected to the syringe 1 by means of LUER-type connector 3. The tube 2 is inserted through a pressure-tight rubber seal 4 in a waste blood holding vessel 5. At the commencement of any particular investigation, the waste blood holding vessel 5 is filled with paraffin oil 6, and the level of blood 7 in the vessel rises during the investigation.

The syringe 1 is received in a syringe mounting block 8, provided with an electrical heating element and thermostat (not shown) to maintain the heating block 8 at a constant temperature of 37° C. The plunger 9 of the syringe 1 is secured by a lock (not shown), to prevent its backward movement, on pressurisation of the blood in the syringe.

The polyethylene tube 2 is threaded through a punching station, generally of the kind described in European Patent Specifiction No. 129425, except for the modification that support is provided for two such polyethylene tubes, and a punching needle 10 is of a sufficient length, and has sufficient movement, to punch through both sides of the tubes 2 of two channels. This is illustrated more clearly in FIG. 2. Needle 10 is attached to a plunger 11, which may be manually actuated, but is preferably actuated by means of a solenoid, or hydraulic or pneumatic actuator. The shank of the punching needle 10 has a diameter of 0.15 mm.

Means (not shown) are provided for enabling the supply of warm saline solution to the punching station, surrounding the tubes, to wash away the blood, as simulated bleeding occurs from holes 12 when the tube is punched. An outlet is provided for the saline solution, and means are provided associated with outlet for causing the saline solution to flow between a light-emitting diode, emitting green light, and a silicon photodiode.

The waste blood holding vessel 5 has three parts, a base 5a, a central tubular part 5b and an upper part 5c. The upper 5c has an opening 19 to which is affixed a pressure transducer 20. An outlet 21 for paraffin oil is also provided in the upper part 5c. A valve 22 is provided for closing outlet 21 from the vessel 5.

Parts 5a, 5b and 5c of the vessel 5 are assembled as a push-fit, and are sealed by "O" rings 24 and 25.

FIG. 3 illustrates schematically an arrangement for supplying an immiscible fluid (paraffin oil) under pressure to the two channels of the instrument.

The apparatus for FIG. 3 includes two pressurisable vessels 30 and 31, and a three-way tap 32. The three-way tap 32 is connected to a low pressure gas supply line 33, and a high pressure gas supply line 34. In the embodiment shown, the pressure in line 33 is arranged to be 60 torr, and that in line 34,360 torr (all pressures referred to herein are gauge pressures) regulators 35 and 36 respectively are provided to maintain the pressure in lines 33 and 34 of the desired level. The three-way valve 32 can be turned between a first position, as shown, in which pressure line 33 is connected directly to pressure vessel 30, via line 38, and pressure line 34 is connected directly to vessel 31, via line 39, and a second position, in which pressure line 34 is connected to both pressure vessels 30 and 31.

Each of vessel 30 and 31 is filled with paraffin oil, and is provided with a respective capillary tube 40, 41 having an internal diameter of approximately 0.18 mm, and a length of approximately 30 cm, to hypodermic needles 42 and 43 respectively.

Means 46 are provided for applying gas under pressure to both pressure regulators 35 and 36. The means 46 may be a pump, or a cylinder of pressurised gas.

In operation of the apparatus, two blood samples are taken from the patient using respective syringes 1 of the two-channels of the apparatus. The syringes 1 are placed in the heating block 8 of the apparatus, and the luer-lock connector 3 is connected to the syringe outlet. The respective tubes 2 are then passed through the piercing station, and through rubber seals 4 of two waste blood holding vessels 5.

Each of the respective syringes 1 is then pierced through its side with a respective hypodermic needle 42, 43, connected to paraffin oil supplies in pressurised vessels 30 and 31 respectively. A pressure of 360 torr is applied to both pressure vessels 30 and 31, which causes paraffin oil to be displaced into the syringes 1 at a rate of approximately 0.1 m per minute. The inflowing paraffin oil prevent sedimentation of red cells in the blood, and displaces the blood through the tubing 2. The pressure at the pressure transducer 20 is observed, until it is steady, with a steady flow of blood entering vessel 5. The tubes 2 of both channels are then simultaneously pierced with the single needle 10, and the pressure at transducer 20 is observed further. A confirmatory check of bleeding through holes 12 is carried out noting the signal received at the silicon photodiode. Bleeding from holes 12 causes the signal to be much reduced, so that on-set and cessation of bleeding can be noted and confirmed.

Figure 4:
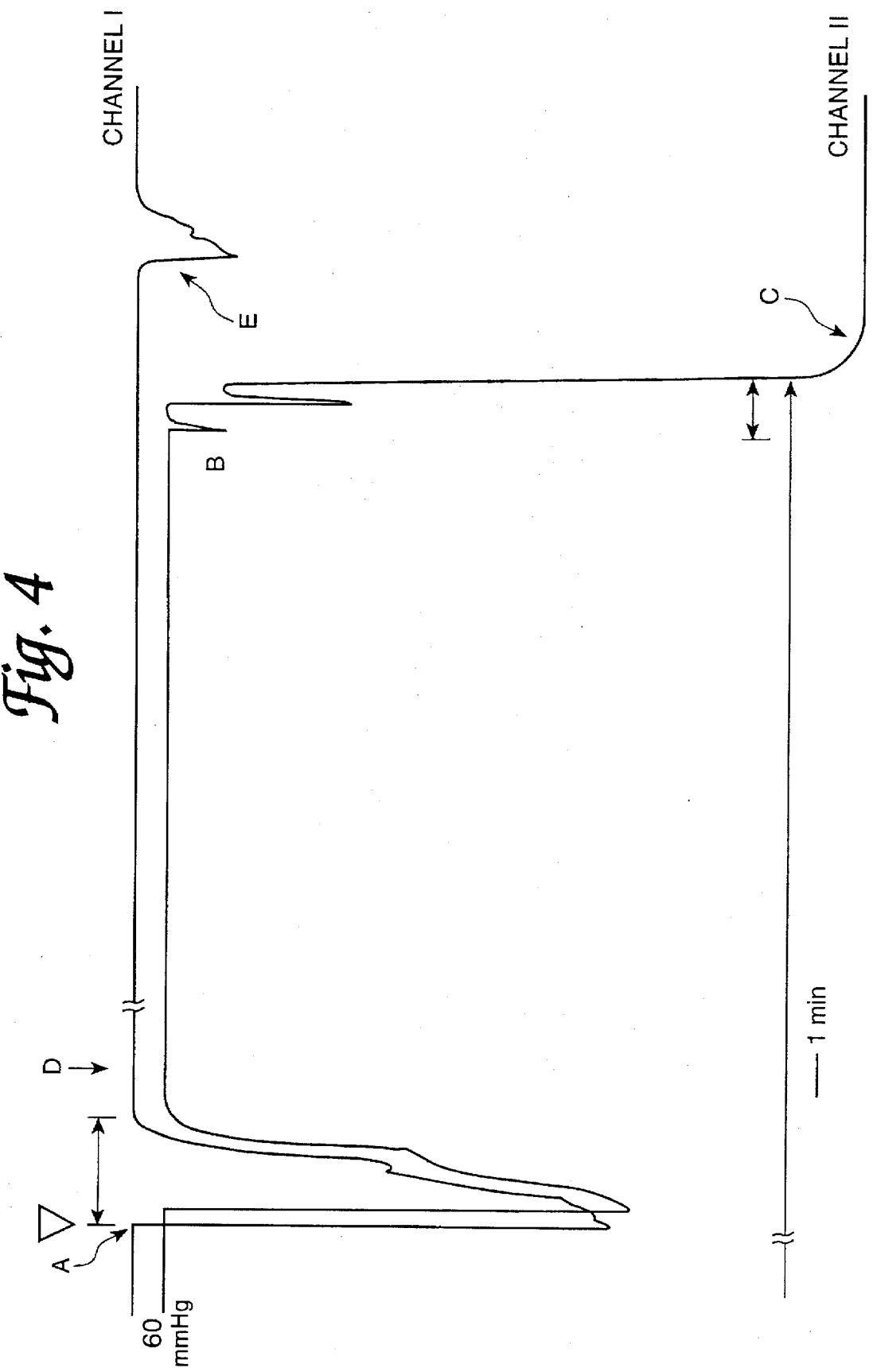
FIG. 4 shows samples of haemostasis, clotting, and thrombolysis traces obtained with the instrument of FIGS. 1 and 2.

FIG. 4 illustrates a typical pressure trace obtained for channels I and II of two-channel apparatus.

In FIG. 4, the trace shown for channel II illustrates the normal process of haemostasis and clotting, when no anti-coagulant is used. Point A is FIG. 4 represents the point at which the tubes 2 are pierced, and as can be seen, the pressure in vessel 5 decreased rapidly, and then slowly rises over a period of approximately two minutes, as haemostasis plugs are formed in holes 12. The pressure in channel II then rises again to its original level of 60 torr, until clotting occurs in tube 2. The on-set of clotting can be seen at point B, and clotting is complete at point C.

In channel I of the apparatus, the progress of haemostasis is identical with that in channel II, but after the haemostasis plugs have been formed, at point D in FIG. 4, an anticoagulant is introduced into the blood in columnar container 1. In practice, this is carried out by introducing into the paraffin oil flowing into the syringe 1 an amount of heparin such as to give a final concentration of 5 U/ml in the blood. Following injection of the anticoagulant, the blood in channel I does not clot, but continues to flow in the tube. To minimize wastage of blood therefore, after sufficient time has been allowed for heparin-containing blood to pass through the system, the valve 22 is closed, and valve 32 is operated, so as to reduce the pressure applied to pressure vessel 30 to 60 torr.

By this method, the progress of the breakdown platelet plugs can be observed, and the effect of various drugs on thrombolysis can also be noted. The breakdown of the haemostasis plugs is shown not only by pressure drop at point E in FIG. 4, but also by the silicon photodiode referred to above. The on-set of bleeding, as sensed by the photodiode, at point A is used to start a electronic clock, when blood appearing in the light pathway reaches a pre-set sensitivity threshold, and decreases the photodiode output below that threshold stops the Quartz clock, to show the elapsed (thrombolysis) time.

Figure 5A:
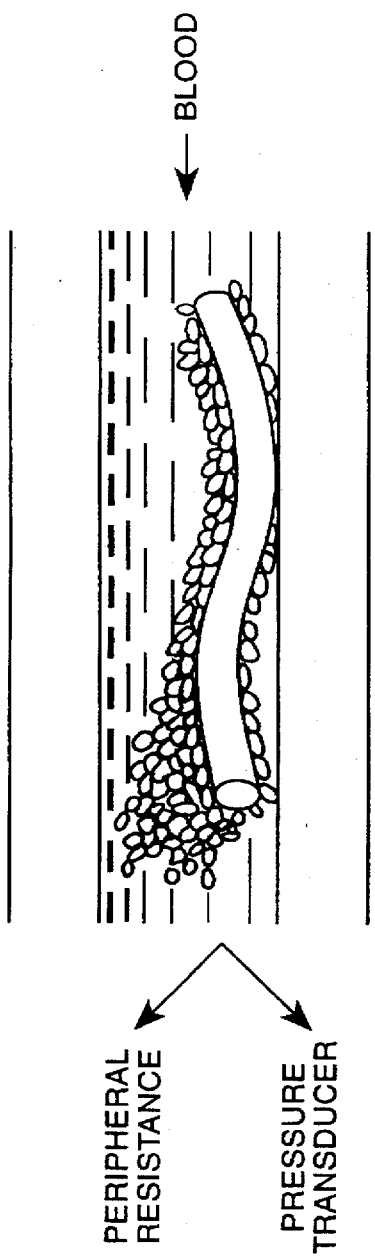
FIG. 5A illustrates the investigation of platelet, collagen interaction.
Figure 5B:
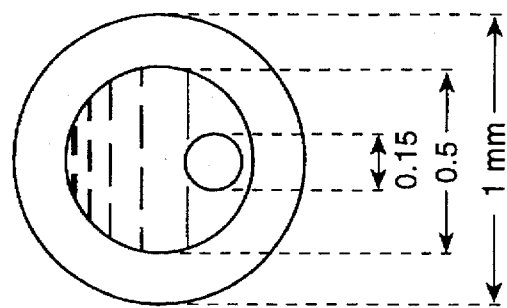
FIG. 5B is a schematic sectional view of the structure of FIG. 5A.

In the embodiment illustrated in FIG. 5A and 5B, the arrangement is generally the same as illustrated in FIG. 1, except that it is not necessary to utilise the needle 10 to punch the tube 2.

As illustrated in FIG. 5A and 5B, a short piece of collagen fibre (surgical catgut), having a diameter of approximately 0.15 mm is placed within the tube 2, before the blood supply is started. Platelets adhere and aggregate on the surface of the catgut, as illustrated in FIG.5A and 5B, and eventually occlude the tube. The rate and extent of the decline of the pressure in the vessel 5 indicate the platelet adhesion to the collagen, and subsequent thrombus formation.

This procedure allows the quantative measurement of platelet function which is most characteristically changed in certain disorders (for example Von Willebrand disease, and by drugs, for example aspirin).

In accordance with the invention, apparatus for the determination of the effects of collagen and the like on thrombus formation may omit the punching means 12. It is preferred however that apparatus in accordance with the invention comprises three substantially identical channels, all as illustrated in FIG. 1. The tubes 2 of two of the channels pass through the punching station, but the other does not, and is intended to receive the piece of collagen fibre.

The invention also provides methods for the determination of clotting, haemostasis and thrombolysis factors of blood, using apparatus as described above.

It is a particular advantage of the apparatus described above that in vivo bleeding is simulated very closely, as well as the subsequent restorative processes, i.e. haemostasis, blood clotting, and clot disolution (thrombolysis). The device disclosed enables the simultaneous measurement of these three factors in a simple, reproducable way, under conditions close to those of haemodynamic stress, and in which a large amount of the blood utilised is saved. Furthermore, non-anticoagulated (native) blood can be utilised for all of these measurements, and all of the various measurements can be made from a blood sample of no more than 5 ml. Furthermore, evaluation of drugs which modify any of the three above processes can be carried out in a setting that is much more physiologically relevant than other in vitro methods used previously in haemostasis research, such as platelet aggregometry.

We claim:

1. Apparatus for the investigation of blood, comprising a columnar reservoir for holding the blood, an elongate tube leading from the reservoir to a waste blood holding vessel, means for measuring blood pressure at a downstream end of said elongate tube, means for introducing into the reservoir a fluid immiscible with blood to displace the blood through the tube, while simultaneously stirring the blood in the columnar reservoir, the means for introducing the immiscible fluid into the columnar reservoir, comprising a pressurisable vessel for the immiscible fluid, means for applying a constant pressure head to the pressurisable container, and a capillary tube leading from the pressurisable vessel to the columnar reservoir, the capillary tube having a resistance to flow substantially greater than that of the tube leading from the columnar reservoir to the waste blood holding vessel.

2. An apparatus for measuring physical properties blood comprising:
at least two reservoirs for holding blood;
at least two elongate tubes connected at one end to a respective reservoir;
a punching station located along said two tubes which simultaneously punches said tubes to form holes of identical size in each tube to permit measurement of blood properties an said elongate tubes;
waste receptacle means connected to remaining ends of said elongate tubes for collecting blood flowing through said elongate tubes;
means for introducing a displacing medium into said reservoirs for stirring the contents of said reservoirs and forcing said blood through said elongate tubes past said punching station, one of said tubes serving as a control sample of blood, permitting a comparison between physical characteristics of blood passing through a remaining tube punctured by said punching station.

3. The apparatus of claim 2 wherein said punching station comprises a punching needle mechanism which simultaneously punctures said elongate tubes, permitting measurement of the clotting and haemostasis of blood flowing through said two elongate tubes.

4. The apparatus of claim 2 further comprising a third reservoir connected through a third elongate tube to said waste receptacle means, said third elongate tube contains a collagen substance for measuring a formation of thrombus on the collagen substance.

5. The apparatus of claim 3 comprising a pressure transducer located at a point downstream of said punching station for measuring pressure changes in one of said elongate tubes following a puncture of said tubes.

6. The apparatus of claim 2 wherein each reservoir is a columnar container comprising a plastic syringe.

7. An apparatus for the investigation of blood comprising:
first and second blood carrying channels, said first channel forming a test channel for subjecting blood to a test condition, the second channel comprising a control channel to compare with said test channel, whereby the effects of a test condition introduced in said test channel on blood flowing therethrough may be monitored, each of said channels comprising:
a columnar reservoir for receiving a sample of blood;
an elongate tube connected at one end a to said columnar reservoir;
a waste receptacle connected to the remaining end of said elongate tube for receiving blood flowing from said columnar reservoir through said elongate tube;
means for introducing in said columnar reservoir a fluid immiscible with blood for stirring blood in said reservoir and to displace the blood through said elongate tube;
pressure monitoring means located adjacent a second end of said elongate tube for measuring the blood pressure at a downstream portion of a respective channel, whereby the relative pressure differences in said first and second blood carrying channels indicates the relative effects of a condition introduced into said test channel on blood flowing therethrough;; and punching means for simultaneously punching holes of the same size in said elongate tubes to simulate bleeding in said elongate tubes, whereby the effects of said test channel on bleeding may be compared with bleeding simulated in said control channel.

8. The apparatus of claim 7 further comprising a third blood carrying channel.

9. An apparatus for measuring physical properties of blood comprising:
at least two reservoirs for holding blood;
at least two elongate tubes connected at one end to a respective reservoir;

a punching station located along said two tubes which simultaneously punches said tubes to form holes of identical size in each tube to permit measurement of blood properties in said elongate tubes;

waste receptacle means connected to remaining ends of said elongated tubes for collecting blood flowing through said elongated tubes;

means for introducing a displacing medium into said reservoirs for stirring the contents of said reservoirs and forcing said blood through said elongated tubes past said punching station, one of said tubes serving as a control sample of blood, permitting a comparison between physical characteristics of blood passing through a remaining tube punctured by said punching station, wherein said means for introducing said displacing medium into said reservoirs comprises:

a pressurizable vessel for holding said immiscible fluid;

means for applying a constant pressure to said pressurizable vessel; and, a capillary tube leading from said pressurizable vessel to said reservoirs, said capillary tube having a resistance to flow substantially greater than that of said elongate tubes, whereby a substantially constant flow through said elongate tubes occurs.

10. An apparatus for measuring physical properties of blood comprising:

at least two reservoirs for holding blood;

at least two elongate tubes connected at one end no a respective reservoir;

a punching station located along said two tubes which simultaneously punches said tubes to form holes of identical size in each tube to permit measurement of blood properties in said elongate tubes;

waste receptacle means connected to remaining ends of said elongated tubes for collecting blood flowing through said elongated tubes;

means for introducing a displacing medium into said reservoirs for stirring the contents of said reservoirs and forcing said blood through said elongated tubes past said punching station, one of said tubes serving as a control sample of blood, permitting a comparison between physical characteristics of blood passing through a remaining tube punctured by said punching station, a three-way tap connected to a source of high pressure and a source of low pressure through first and second regulators;

first and second pressurizable vessels, said first vessel having a first inlet connected to said three-way tap, said second vessel having an inlet connected to said source of high pressure; and, first and second capillary tubes connecting said first and second vessels to said reservoirs.

11. Apparatus for the investigation of blood, comprising a columnar reservoir for holding the blood, an elongate tube leading from the reservoir to a waste blood holding vessel, means for measuring blood pressure at a downstream end of said elongate tube, means for introducing into the reservoir a fluid immiscible with blood to displace the blood through the tube, while simultaneously stirring the blood in the columnar reservoir, a valve for closing an outlet of the waste blood holding vessel, so that after anticoagulated blood has passed through the whole of the elongate tube, the valve can be closed, maintaining the pressure in the system without a less of blood therefrom, including means for applying a reduced pressure to the displacement fluid, after closure of the valve, wherein the means for applying the reduced pressure comprises two pressurizable containers, means for pressurizing the containers to different pressures, and means for alternatively switching the pressure from the two containers to drive the displacement fluid.

12. Apparatus for the investigation of blood, comprising a columnar reservoir for holding the blood, an elongate tube leading from the reservoir to a waste blood holding vessel, means for measuring blood pressure at a downstream end of said elongate tube, means for introducing into the reservoir a fluid immiscible with blood to displace the blood through the tube, while simultaneously stirring the blood in the columnar reservoir, a valve for closing an outlet of the waste blood holding vessel, so that after anticoagulated blood has passed through the whole of the elongate tube, the valve can be closed, maintaining the pressure in the system without a loss of blood therefrom, wherein the means for introducing the immiscible fluid into the columnar reservoir comprises a pressurizable vessel for the immiscible fluid, means for applying a constant pressure head to said pressurizable vessel, and means for reducing the pressure applied to the pressurizable vessel when the valve is closed.

* * * * *